United States Patent
Stokes et al.

(10) Patent No.: US 6,494,617 B1
(45) Date of Patent: Dec. 17, 2002

(54) STATUS DETECTION APPARATUS AND METHOD FOR FLUID-FILLED ELECTRICAL EQUIPMENT

(75) Inventors: Edward B. Stokes, Niskayuna, NY (US); Steven H. Azzaro, Schenectady, NY (US); Thomas G. O'Keeffe, Farmington, CT (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/302,299

(22) Filed: Apr. 30, 1999

(51) Int. Cl.[7] .................... G01K 13/00; H01F 27/00
(52) U.S. Cl. ................ 374/152; 374/137; 374/142; 374/166; 336/57
(58) Field of Search ................ 374/101, 110, 374/142, 137, 152, 166; 336/57, 58, 61; 73/19.01; 340/632

(56) References Cited

U.S. PATENT DOCUMENTS

| | | | |
|---|---|---|---|
| 2,795,779 A | 6/1957 | Book | 340/248 |
| 2,917,701 A | * 12/1959 | Salton | 336/57 |
| 3,144,770 A | * 8/1964 | Sheely | 374/152 |
| 3,680,359 A | 8/1972 | Lynch | 73/27 |
| 3,797,314 A | * 3/1974 | Lampe et al. | 374/152 |
| 3,821,605 A | 6/1974 | Pendrak | 317/14 |
| 3,832,600 A | 8/1974 | Specht | 317/14 |
| 3,844,160 A | 10/1974 | Yamaoka | 73/19 |
| 3,855,503 A | 12/1974 | Ristuccia | 317/27 |
| 3,864,628 A | 2/1975 | Klass et al. | 324/71 |
| 3,866,460 A | 2/1975 | Pearce, Jr. | 73/19 |
| 3,927,570 A | * 12/1975 | Hedvall et al. | 374/152 |
| 3,960,017 A | * 6/1976 | Romanowski | 374/152 |
| 4,058,373 A | 11/1977 | Kurz et al. | 55/16 |
| 4,112,737 A | 9/1978 | Morgan | 73/23 |
| 4,129,501 A | 12/1978 | Haynes | 210/23 |

(List continued on next page.)

FOREIGN PATENT DOCUMENTS

WO  WO9833066 A  7/1998

OTHER PUBLICATIONS

James L. Kirtley, Jr. et al. "Monitoring the Health of Power Transformers", IEEE Computer Applications in Power, Jan. 1996, pp. 18–23.

(List continued on next page.)

Primary Examiner—Diego Gutierrez
Assistant Examiner—Madeline Gonzalez
(74) Attorney, Agent, or Firm—Hunton & Williams

(57) ABSTRACT

A status detection apparatus for electrical equipment includes a plurality of distributed multiparameter sensors in a containment vessel or other fluid filled region of the electrical equipment. The sensors are capable of providing data relating to plural parameters of the fluid simultaneously at different positions in the fluid. The data provided by the sensors can be processed to permit localization of incipient faults or can indicate other operating states when combined with known flow data of the fluid through the electrical equipment. A method for detecting status of electrical equipment includes sensing parameters simultaneously at multiple locations in the fluid and determining operating status based on the sensed parameters.

19 Claims, 1 Drawing Sheet

U.S. PATENT DOCUMENTS

| | | | | |
|---|---|---|---|---|
| 4,145,679 | A | * 3/1979 | Mitchell, Jr. | 336/57 |
| 4,179,927 | A | * 12/1979 | Saaski | 374/152 |
| 4,201,089 | A | * 5/1980 | Felber et al. | 374/152 |
| 4,218,298 | A | 8/1980 | Shimada et al. | 204/195 |
| 4,232,551 | A | * 11/1980 | Pierce | 336/57 |
| 4,236,404 | A | 12/1980 | Ketchum et al. | 73/19 |
| 4,347,732 | A | 9/1982 | Leary | 73/13 |
| 4,354,308 | A | 10/1982 | Shimada et al. | 29/571 |
| 4,394,635 | A | * 7/1983 | Foss | 336/61 |
| 4,402,211 | A | 9/1983 | Sugawara et al. | 73/19 |
| 4,446,420 | A | 5/1984 | Drouet | 324/52 |
| 4,474,051 | A | * 10/1984 | Fukuda et al. | 73/19.01 |
| 4,483,631 | A | * 11/1984 | Kydd | 374/141 |
| 4,508,461 | A | 4/1985 | Lambert | 374/161 |
| 4,517,468 | A | 5/1985 | Kemper et al. | 290/52 |
| 4,549,817 | A | * 10/1985 | Felber | 374/152 |
| 4,644,479 | A | 2/1987 | Kemper et al. | 364/550 |
| 4,654,806 | A | 3/1987 | Poyser et al. | |
| 4,730,479 | A | 3/1988 | Pyke et al. | 73/23 |
| 4,754,405 | A | 6/1988 | Foster | 364/557 |
| 4,763,514 | A | 8/1988 | Naito et al. | 73/19 |
| 4,772,978 | A | 9/1988 | Oura et al. | 361/36 |
| 4,823,224 | A | 4/1989 | Hagerman et al. | 361/37 |
| 4,827,487 | A | 5/1989 | Twerdochlib | 374/152 |
| 4,830,513 | A | 5/1989 | Grego | 374/131 |
| 4,890,478 | A | 1/1990 | Claiborne et al. | 73/19 |
| 4,931,851 | A | 6/1990 | Sibbald et al. | 357/25 |
| 4,944,178 | A | 7/1990 | Inoue et al. | 73/19.3 |
| 4,947,104 | A | 8/1990 | Pyke | 324/71.5 |
| 4,953,387 | A | 9/1990 | Johnson et al. | 73/25.03 |
| 4,964,125 | A | 10/1990 | Kim | 371/15.1 |
| 5,018,075 | A | 5/1991 | Ryan et al. | 364/513 |
| 5,035,511 | A | 7/1991 | Berthold | 374/124 |
| 5,062,092 | A | 10/1991 | Siryj et al. | 369/38 |
| 5,078,437 | A | 1/1992 | Borgmeyer et al. | 292/206 |
| 5,099,436 | A | 3/1992 | McCown et al. | 364/550 |
| 5,113,277 | A | 5/1992 | Ozawa et al. | 359/127 |
| 5,123,017 | A | 6/1992 | Simpkins et al. | 371/15.1 |
| 5,127,962 | A | 7/1992 | Inoue et al. | 134/22.12 |
| 5,132,920 | A | 7/1992 | Bellows et al. | 364/551.01 |
| 5,133,046 | A | 7/1992 | Kaplan | 395/61 |
| 5,191,206 | A | 3/1993 | Boiarski et al. | 250/227.14 |
| 5,192,174 | A | 3/1993 | Hartmann | 409/283 |
| 5,225,395 | A | 7/1993 | Tashiro et al. | 505/1 |
| 5,255,208 | A | 10/1993 | Thakore et al. | 364/551.01 |
| 5,257,528 | A | 11/1993 | Degouy et al. | 73/53.01 |
| 5,261,747 | A | * 11/1993 | Deacutis et al. | 374/137 |
| 5,286,109 | A | 2/1994 | Hanscombe et al. | 374/119 |
| 5,396,172 | A | 3/1995 | Lat et al. | 324/547 |
| 5,400,018 | A | 3/1995 | Scholl et al. | 340/825.54 |
| 5,408,999 | A | 4/1995 | Singh et al. | 128/634 |
| 5,414,645 | A | 5/1995 | Hirano | 364/551.01 |
| 5,417,821 | A | 5/1995 | Pyke | 204/153.1 |
| 5,445,347 | A | 8/1995 | Ng | 246/169 |
| 5,448,772 | A | 9/1995 | Grandfield | 455/333 |
| 5,493,729 | A | 2/1996 | Nigawara et al. | 395/61 |
| 5,499,313 | A | 3/1996 | Kleinerman | 385/123 |
| 5,534,853 | A | 7/1996 | Pioch | 340/646 |
| 5,541,832 | A | 7/1996 | Nakajima et al. | 364/148 |
| 5,566,092 | A | 10/1996 | Wang et al. | 364/551.02 |
| 5,586,305 | A | 12/1996 | Eidson et al. | 395/500 |
| 5,591,321 | A | 1/1997 | Pyke | 205/787 |
| 5,659,126 | A | 8/1997 | Farber | 73/19.02 |
| 5,684,297 | A | 11/1997 | Tardy | 250/227.14 |
| 5,696,863 | A | 12/1997 | Kleinerman | 385/123 |
| 5,773,709 | A | 6/1998 | Gibeault et al. | 73/25.01 |
| 5,775,808 | A | * 7/1998 | Pan | 374/137 |
| 5,783,152 | A | 7/1998 | Nave | 422/82.06 |
| 5,806,011 | A | 9/1998 | Azzaro et al. | 701/99 |
| 5,845,272 | A | 12/1998 | Morjaria et al. | 706/50 |
| 6,157,282 | A | * 12/2000 | Hopkinson | 336/57 |
| 6,217,211 | B1 | * 4/2001 | Hesky | 374/137 |

OTHER PUBLICATIONS

H. Sundgren, "Artificial Neural Networks and Gas Sensor Arrays: Quantification of Individual Components in a Gas Mixture", Meas. Sci. Technology 2 (1991) 464–469.

GE Corporate Information Research Center "Articles About the Micromonitors Invention:" Literature Search Services, Micromonitors Inc., Sep. 1, 1998.

GE Corporate Information Research, Literature Search Services: "Patent Search: SYPROTEC", Sep. 9, 1998 pp. 1–11.

J.W. Harley Inc. "Proceedings of the Thirteenth Harley On–Line Monitoring Users' Conference", Jan. 15–16, 1997, Oklahoma City, Oklahoma.

* cited by examiner

STATUS DETECTION APPARATUS AND METHOD FOR FLUID-FILLED ELECTRICAL EQUIPMENT

BACKGROUND OF THE INVENTION

The invention relates generally to electrical equipment. More particularly, the invention relates to a status detection apparatus for determining operating status of electrical equipment in real time through measurement of various parameters of fluid surrounding components of the electrical equipment, and to electrical equipment incorporating the status detection apparatus.

Electrical equipment, particularly medium-voltage or high-voltage electrical distribution equipment, require a high degree of electrical and thermal insulation between components thereof. Accordingly, it is well known to encapsulate components of electrical equipment, such as coils of a transformer, in a containment vessel and to fill the containment vessel with a fluid. The fluid facilitates dissipation of heat generated by the components and can be circulated through a heat exchanger to efficiently lower the operating temperature of the components. The fluid also serves as electrical insulation between components or to supplement other forms of insulation disposed around the components, such as cellulose paper or other insulating materials. Any fluid having the desired electrical and thermal properties can be used. Typically, electrical equipment is filled with an oil, such as castor oil or mineral oil, or a synthetic "oil" such as chlorinated diphenyl, silicone oil, vegetable oil, or sulfur hexafluoride.

Often electrical distribution equipment is used in a mission critical environment in which failure can be very expensive or even catastrophic because of a loss of electric power to critical systems. Also, failure of electrical distribution equipment ordinarily results in a great deal of damage to the equipment itself and surrounding equipment thus requiring replacement of expensive equipment. Further, such failure can cause injury to personnel due electric shock, fire, or explosion. Therefore, it is desirable to monitor the status of electrical equipment to predict potential failure of the equipment through detection of incipient faults and to take remedial action through repair, replacement, or adjustment of operating conditions of the equipment.

A known method of monitoring the status of fluid-filled electrical equipment is to monitor various parameters of the fluid. For example, the temperature of the fluid and the total combustible gas (TCG) in the fluid is known to be indicative of the operating state of fluid-filled electrical equipment. Therefore, monitoring these parameters of the fluid can provide an indication of any incipient faults in the equipment. For example, it has been found that carbon monoxide and carbon dioxide increase in concentration with thermal aging and degradation of cellulosic insulation in electrical equipment. Hydrogen and various hydrocarbons (and derivatives thereof such as acetylene and ethylene) increase in concentration due to hot spots caused by circulating currents and dielectric breakdown such as corona and arcing. Concentrations of oxygen and nitrogen indicate the quality of the gas pressurizing system employed in large equipment, such as transformers. Accordingly "dissolved gas analysis" (DGA) has become a well accepted method of discerning incipient faults in fluid-filled electric equipment.

In known DGA methods, an amount of fluid is removed from the containment vessel of the equipment through a drain valve. The removed fluid is then subjected to testing for dissolved gas in a lab or by equipment in the field. This method of testing is referred to herein as "off-line" DGA. Since the gases are generated by various known faults, such as degradation of insulation material or other portions of electric components in the equipment, turn-to-turn shorts in coils, overloading, loose connections, or the like, various diagnostic theories have been developed for correlating the quantities of various gases in fluid with particular faults in electrical equipment in which the fluid is contained.

However, since known methods of off-line DGA require removal of fluid from the electric equipment, known methods do not, 1) yield localized position information relating to any fault in the equipment, 2) account for spatial variations of gases in the equipment, and 3) provide real time data relating to faults. If analysis is conducted off site, results may not be obtained for several hours. Incipient faults may develop into failure of the equipment over such a period of time. MICROMONITORS, INC™ and SYPROTEC™ have each developed a gas sensor which resides in the drain valve, or other single locations, of a transformer and overcomes some of the limitations of off-line DGA. However, location data relating to a fault is not discernable with such a device because it is located in one predefined position and does not provide any indication of the position of the source of the gas, i.e., the fault.

Various multiparameter sensors are known for detecting parameters such as temperature, acidity, concentrations of various gases, degree of polymerization or the like. For example, U.S. Pat. No. 5,591,321 discloses an array of semiconductor diode sensors, each for detecting a particular parameter. Also, distributed arrays of sensors have been used in various applications for detecting a single parameter, such as temperature. U.S. Pat. Nos. 5,191,206, 5,696,863, and 5,499,313 are exemplary of distributed temperature sensors. U.S. Pat. No. 4,827,487 discloses a distributed temperature sensor for electric motor stator windings. Distributed multiparameter sensing has been used in process control as exemplified by U.S. Pat. No. 5,586,305. U.S. Pat. No. 4,654,806 discloses an apparatus for monitoring transformers including a top oil temperature sensor and a hot spot temperature sensor located in a known hot spot of the transformer. However, this apparatus falls short of providing data required to localize faults.

Known processes and apparatus do not provide accurate, real-time data indicating the type and location of incipient faults in fluid filled electrical equipment. Also, since known processes do not account for spatial variations of parameters in fluid filled electric equipment, the accuracy of fault determinations with known processes is reduced.

SUMMARY OF THE INVENTION

The invention is directed toward a status detection apparatus, for electrical equipment comprising a plurality of distributed multiparameter sensors in a containment vessel or other fluid filled region of the electrical equipment. The sensors are capable of providing data relating to plural parameters of the fluid simultaneously at different positions in the fluid filled region. The data provided by the sensors can be processed to permit localization of incipient faults when combined with known flow data of the fluid through the electrical equipment.

A first aspect of the invention is an electrical apparatus, comprising a containment vessel configured to contain a fluid, at least one electrical component disposed in the containment vessel, and distributed multiparameter sensors disposed in the containment vessel. A second aspect of the invention is a status detection apparatus for detecting faults in electrical equipment of the type having a containment vessel configured to contain a fluid, and at least one electrical component disposed in the containment vessel. The status detection apparatus comprises distributed multiparameter sensors disposed in the containment vessel and configured to generate data indicative of sensed parameters, a data acquisition device for determining operating status of the electrical equipment, and means for conducting signals from the multiparameter sensors to the data acquisition device. A third aspect of the invention is an electrical transformer comprising a containment vessel, a transformer core having coils thereon, and distributed multiparameter sensors disposed in the containment vessel. A fourth aspect of the invention is a method of detecting operating status in electrical equipment of the type having a containment vessel, at least one electrical component in the containment vessel, and a fluid in the containment vessel surrounding the at least one electrical component. The method comprises the steps of sensing plural parameters of the fluid at plural sensing locations in the fluid simultaneously and determining operating status of the electrical equipment based on the results of the sensing step.

BRIEF DESCRIPTION OF THE DRAWING

The present invention can be more fully understood upon reading the following detailed description in conjunction with the accompanying drawing in which.

DETAILED DESCRIPTION OF THE PREFERRED EMBODIMENT

Figure 1:
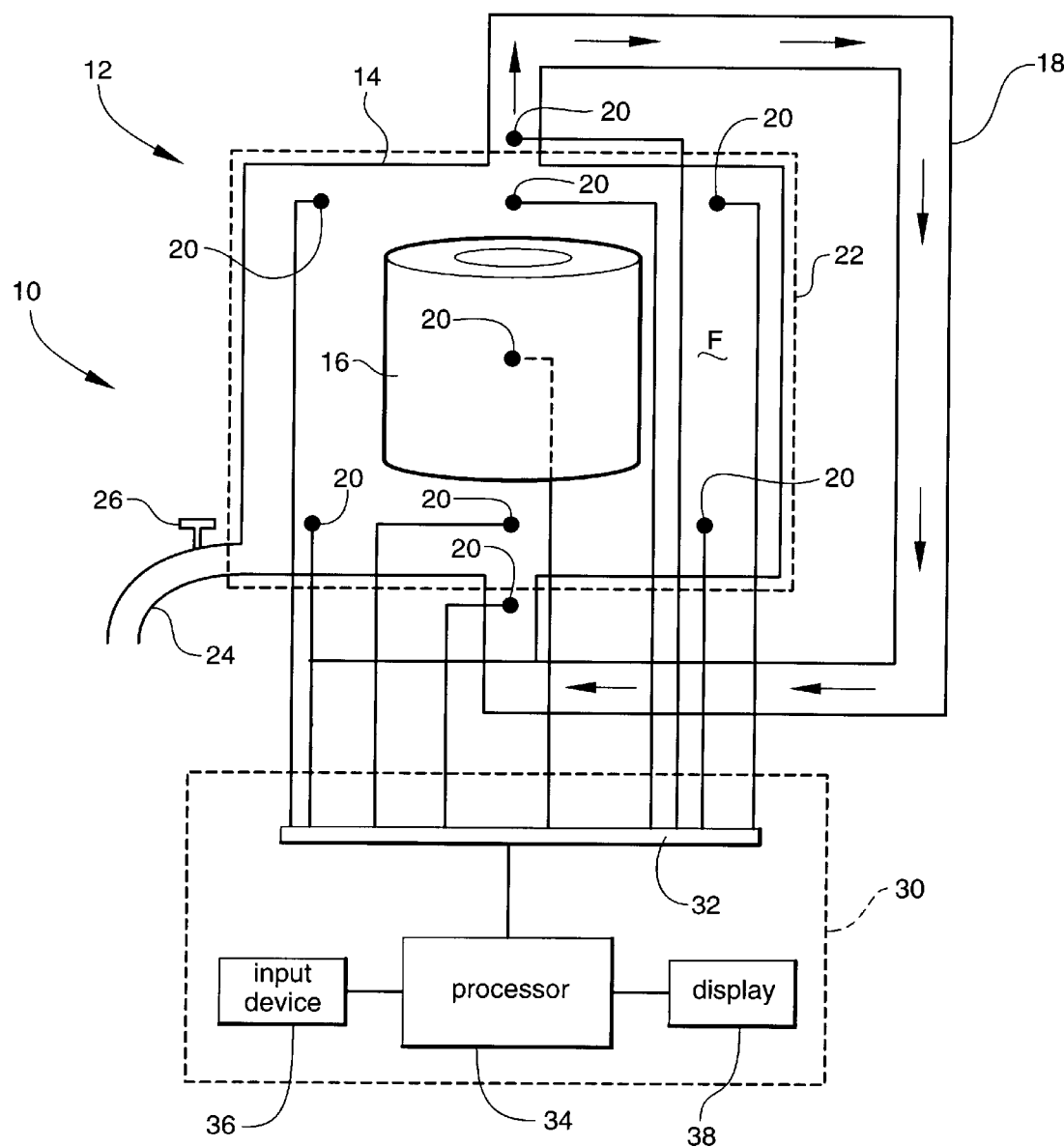
FIG. 1 is a schematic illustration of a preferred embodiment of the invention.

FIG. 1 illustrates a preferred embodiment of the invention. Status detection system 10 comprises electrical equipment 12, an electrical distribution transformer in the preferred embodiment, and data acquisition device 30. Electrical equipment 12 comprises electrical components 16, including a core and coils/windings of the transformer, containment vessel 14 surrounding components 16, radiator 18 in communication with containment vessel 14, drain port 24, and valve 26 for selectively sealing drain port 24. Containment vessel 14 is adapted to contain fluid F, such as oil, for cooling components 16. Fluid F circulates through containment vessel 14 and radiator 18 as schematically indicated by arrows in FIG. 1. Radiator 18 serves as a heat exchanger to cool fluid F and to thereby conduct heat away from components 16. Radiator 18 can include any known form of pipes, conduits, heat exchanging surfaces, cooling elements, pumps, or the like. While radiator 18 in the preferred embodiment is illustrated schematically as having pipes or conduits separate from containment vessel 14, sides or other portions of containment vessel 14 can serve as the radiator to conduct heat away from fluid F and thus a separate radiator is not required. Cooling can be accomplished through thermal convection, thermal conduction, molecular convection of fluid F, or in any other manner.

A plurality of multiparameter sensors 20 are spatially distributed throughout containment vessel 14 and/or radiator 18 to sense various parameters of fluid F. In the preferred embodiment, sensors 20 are in contact with fluid F. However, the invention requires only that the sensors 20 be capable of measuring parameters of fluid F. Accordingly, the sensors can be in a contact or non contact relationship with fluid F depending on the type of sensors used, as discussed in greater detail below. For example, sensors 20 can be positioned remotely from fluid F and can have sensing elements disposed in fluid F. Alternatively, sensors 20 can be entirely remote from fluid F and can monitor parameters in fluid F from a distance, such as through optical means or the like. Note that in the preferred embodiment, sensors 20 are disposed throughout containment vessel 14, including a passage defined through component 16, and in portions of radiator 18. However, sensors 20 can be disposed at any location and can sense parameters of fluid F at any location as dictated by the type, size, and shape of the electrical equipment, and any other details of the practical application. Preferably, sensors 20 are disposed at positions defining a three-dimensional grid within equipment 12.

The phrase "distributed sensors" as used herein refers to a sensor or sensors that can measure a parameter simultaneously at more than one location. For example, a distributed array of sensors can be plural sensors distributed spatially. The phrase "multiparameter sensor" as used herein refers to a sensor capable of measuring more than one parameter at a single location. A multiparameter sensor can in fact be plural single parameter sensors in close spatial relationship. The phrase "distributed multiparameter sensors" therefore refers to a sensor or sensors capable of measuring more than one parameter simultaneously at each of more than one location. The multiparameter sensors 20 of the invention can be plural spatially distributed of discrete multiparameter sensors or a continuous sensing layer or the like for which the output is decoded, by time division multiplexing for example, to produce an output for plural locations along the layer.

Sensors 20 can be fixedly disposed in containment vessel 14 and/or radiator 18. Alternatively, sensors 20 can be removably disposed in desired locations by being selectively inserted through sensor ports or other openings formed through walls of containment vessel 14 and/or radiator 18. Of course, in the latter configuration, proper seals should be provided to prevent leakage of fluid F from containment vessel 14 and/or radiator 18. Sensors 20 can be of any appropriate type. For example, each sensor 20 can be one or more of metal insulator semiconductor diode sensors, fiber optic probes, acoustic or optical waveguides, bimetal sensors, thin film sensors, or any other appropriate sensor or transducer for measuring the parameters noted below. If sensor 20 is electric or electronic in nature and disposed inside high EM field region 22 (indicated by a dotted line in FIG. 1), sensors 20 must have the proper electrical shielding. Optical or other types of sensors need not be electrically shielded regardless of location. Sensors 20 generate data or signals indicative of various parameters of fluid F.

Data acquisition device 30 comprises data bus 32, processor 34, input device 36, and display 38. Sensors 20 are communicatively coupled to data bus 32 through appropriate conducting means. For example, if sensors 20 are electronic or produce electronic signals, electric conductors can extend from sensors 20 to an exterior of equipment 12. The conductors can terminate at any appropriate terminal strip, connector or the like, for connection to data acquisition device 30. Coupling between sensors 20 and data acquisition device 30 can be accomplished by wires, fiber optic strands, radio frequency devices, or in any other known manner. Data bus 32 can receive signals from sensors 20 in any known manner through any known interface. For example, data acquisition device 30 can be a personal computer and data bus 32 can receive signals through a serial port, parallel port, universal serial bus port, or the like. Any appropriate transducer or signal processing circuitry can be used to interface sensors 20 to data acquisition device 30. Data bus 32 can utilize any appropriate type of hardware and/or software protocols for receiving data or signals from sensors 20. Data bus 32 can be any appropriate type of device for carrying data or signals from sensors 32, such as a standard ISA bus, DCI bus, GPIB bus, or a simple terminal strip. Data acquisition device 30 can communicate with sensor 12 over a remote or local communication link.

Data acquisition device 30 can be any device capable of acquiring signals or data from sensors 20 and taking appropriate action thereon, such as sounding an alarm. For example, data acquisition device 30 can be a personal computer, an industrial programmable controller, or any other type of logic device. Processor 34 can be any type of microprocessor based device, hardwired electric components, a dedicated logic device of any type, or the like. Processor 34 can include memory devices such as random access memory, magnetic memory, optical memory, or the like, for storing a control program, data, threshold values, alarm limits, and the like. Input device 36 can be any type of keyboard, switch or switches, or any other device for providing settings parameters or instructions to controller 34. Input device can be omitted. Display 38 can be any type of display for indicating operating status, such as an LCD or CRT display, a pilot lamp or series of pilot lamps, an audible alarm, or the like. Sensors 20 can be coupled directly to a display, such as a visible or audible alarm or indicator and, in such a case, processor 34 can be omitted.

In operation, containment vessel 14 is fully or partially filled with fluid F, such as oil. In this state, sensors 20 are in contact with or otherwise can sense various parameters in fluid F at plural locations. For example, the temperature of fluid F and the content of various gases, such as hydrogen, acetylene, carbon, monoxide, and ethylene are indicative of operational status of equipment 12, as discussed above. Of course, any parameter which is helpful in determining the operational status of equipment 12 can be sensed by all or some of sensors 20. Sensors 20 are capable of measuring plural parameters, i.e. are multiparameter sensors, and are distributed throughout fluid F, or configured to measure the plural parameters throughout fluid F, in a dimensional grid to provide a real time three-dimensional map of multiple parameters in fluid F. For example, temperature and various gas concentrations can be measured simultaneously at different positions in the spatial grid and the measurement data or signals can be acquired by data acquisition system 30 in a known manner to determine an operating state of equipment 12, used to alter operation of equipment 12, or to take other appropriate action.

Such a three-dimensional map, when combined with well known fluid flows for the particular equipment, and temperature dependant diffusion properties for the particular gasses being detected, will allow location of incipient faults within the level of resolution of the spatial grid defined by the sensing positions in fluid F of sensors F. The resolution can be increased by placing sensors 20 closer together or otherwise making the sensing positions closer together, and providing more sensors 20 if necessary, to increase the accuracy of the position detection of faults. The redundancy of sensors 20 allows sensing of parameters even when one or a few of sensors 20 fails. The time evolution of the three-dimensional map can provide additional information relating to the types of gas present in fluid F because the known diffusion rates of various gases are different.

The invention can be applied to any fluid filled electrical equipment. Any desired parameters can be detected. Sensor data or signals can be processed in any way to provide indication of incipient faults or other status of the electrical equipment based on empirical or mathematical models. The data acquisition device can be local, i.e closely situated with respect to the electrical equipment, or remote, i.e., located at a remote location with respect to the electrical equipment. Histories of the values of the various parameters can be compiled to assist further in fault determination. The various sensors can be polled at regular intervals and the intervals can be increased at times of heavy load on the equipment or upon indication of an abnormal state of the equipment. The load condition of the equipment can be detected and correlated to temperature and gas detection. Other parameters such as fluid pressure and viscosity, noise generated by the equipment, and the like can be detected also. The invention can be used to determine and/or check fluid flow models of electrical equipment by injecting gas or other detectable substances into the fluid and determining the change in the three-dimensional map of the substance in the fluid over time. The sensors or sensing locations do not necessarily have to define a grid. Any appropriate spatial distribution can be used to sense parameters at desired positions.

What is claimed is:

1. An electrical apparatus comprising:

a containment vessel;

at least one electrical component disposed in said containment vessel;

a thermoelectric insulating fluid disposed in the containment vessel and surrounding the at least one electrical component; and distributed multiparameter sensors disposed in said containment vessel in locations corresponding to a three-dimensional map of said containment vessel.

2. An electrical apparatus as recited in claim 1, further comprising a radiator coupled to said containment vessel, said radiator being operative to remove heat from said fluid, at least one of said multiparameter sensors being disposed in said radiator.

3. An electrical apparatus as recited in claim 2, wherein said fluid comprises one of castor oil, mineral oil, silicone oil, sulfur hexafluoride, vegetable oil, and chlorinated diphenyl.

4. An electrical apparatus as recited in claim 3, further comprising means for conducting signals from said sensors to an exterior of said containment vessel.

5. An electrical apparatus as recited in claim 4, wherein each of said sensors is configured to detect temperature of the fluid at a respective sensing position in the fluid, and gas concentration in the fluid at the same sensing position.

6. An electrical apparatus as recited in claim 5, wherein each of said sensors detects a concentration of at least one of hydrogen, carbon monoxide, carbon dioxide, oxygen, nitrogen, hydrocarbons, and hydrocarbon derivatives.

7. An electrical apparatus, as recited in claim 5, wherein said sensing positions define a three-dimensional grid.

8. An electrical apparatus as recited in claim 1, wherein said sensors are disposed at positions defining a three-dimensional grid.

9. An electrical apparatus as recited in claim 1, further comprising:

a data acquisition device for determining operating status of said at least one electrical component based on data output by said multiparameter sensor; and means for conducting signals from said multiparameter sensors to said data acquisition device.

10. An electrical apparatus as recited in claim 1, wherein said at least one electrical component comprises a core and coils of an electrical distribution transformer.

11. An electrical transformer comprising:

a containment vessel configured to contain a fluid;

at least one core disposed in said containment vessel and having coils thereon; and distributed multiparameter sensors disposed in said containment vessel in locations corresponding to a three-dimensional map of said containment vessel.

12. An electrical transformer as recited in claim 11 further comprising a radiator coupled to said containment vessel, said radiator being operative to remove heat from said fluid, at least one of said multiparameter sensors being disposed in said radiator.

13. An electrical transformer as recited in claim 12, wherein said fluid comprises one of castor oil, mineral oil, silicone oil, sulfur hexafluoride, vegetable oil and chlorinated diphenyl.

14. An electrical transformer as recited in claim 13, further comprising means for conducting signals from said sensors to an exterior of said containment vessel.

15. An electrical transformer as recited in claim 14, wherein each of said sensors is configured to detect temperature of the fluid at a respective sensing position, and gas concentration in the fluid at the same sensing position.

16. An electrical transformer as recited in claim 15, wherein each of said sensors detects a concentration of at least one of hydrogen, carbon monoxide, carbon dioxide, oxygen, nitrogen, hydrocarbons, and hydrocarbon derivatives.

17. An electrical transformer as recited in claim 15, wherein said sensing positions define a three-dimensional grid.

18. An electrical transformer as recited in claim 11, wherein said sensors are disposed at positions defining a three-dimensional grid.

19. An electrical apparatus comprising:

a containment vessel;

at least one electrical component disposed in said containment vessel;

a thermoelectric insulating fluid disposed in the containment vessel and surrounding the at least one electrical component; and sensors disposed in sensing positions within said containment vessel, the sensing positions defining a grid.

* * * * *